United States Patent [19]

Nezot et al.

[11] 4,450,169

[45] May 22, 1984

[54] INSECTICIDAL ESTERS

[75] Inventors: Francois Nezot, Thiais; Pierre Girault, Paris; Jean Tessier, Vincennes; Jacques Martel, Bondy, all of France

[73] Assignee: Roussel Uclaf, Paris, France

[21] Appl. No.: 352,257

[22] Filed: Feb. 25, 1982

[30] Foreign Application Priority Data

Feb. 26, 1981 [FR] France .................................. 81 03831

[51] Int. Cl.³ .................. C07D 417/12; A61K 31/425; C07D 277/30; C07D 277/34
[52] U.S. Cl. ...................................... 424/270; 424/269; 548/128; 548/129; 548/187; 548/204
[58] Field of Search .................. 548/204, 187; 424/270

[56] References Cited

FOREIGN PATENT DOCUMENTS 41021 12/1981 European Pat. Off. ............ 424/305
2719561 11/1977 Fed. Rep. of Germany ...... 548/204

OTHER PUBLICATIONS

Sota, Agr. & Bio. Chem. 36, 2287 (1972).

Primary Examiner—Robert Gerstl
Attorney, Agent, or Firm—Charles A. Muserlian

[57] ABSTRACT

Novel esters of the formula

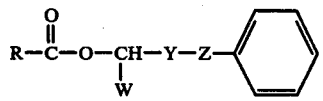

wherein R is selected from the group consisting of

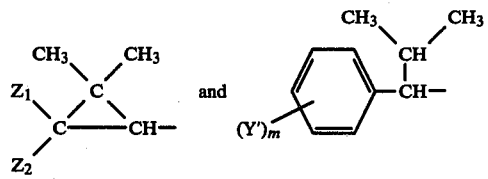

W is selected from the group consisting of hydrogen and —CN, Z is selected from the group consisting of —CH$_2$— and —O—, and is attached to a carbon atom included between a nitrogen and the sulfur atom of Y and Y is selected from the group consisting of thiazolyl or thiadiazolyl connected to

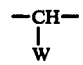

at one of its available positions.

3 Claims, No Drawings

INSECTICIDAL ESTERS

STATE OF THE ART

German Pat. No. 2,719,561 describes compounds of the formula

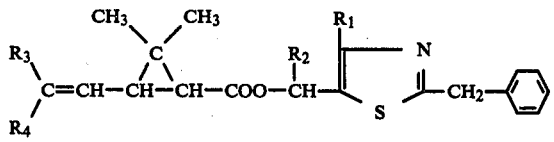

wherein $R_1$ is hydrogen, $R_2$ is hydrogen, —CN or —C≡CH, $R_3$ is fluorine, chlorine, bromine or —CH$_3$ and $R_4$ is fluorine, chlorine or bromine. Chem. Abs., Vol. 78 (1973) No. 17, p. 111193 v which relates to Agr. Biol. Chem., Vol. 36(13) (1972), p. 2287–2296 describes compounds of the formula

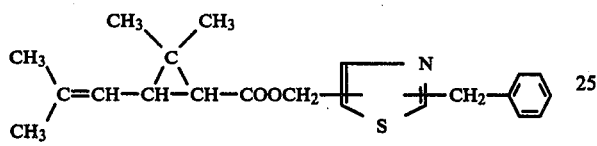

Pesticide Sciences, Vol. 7 (1976), p. 258–266 describes the compound

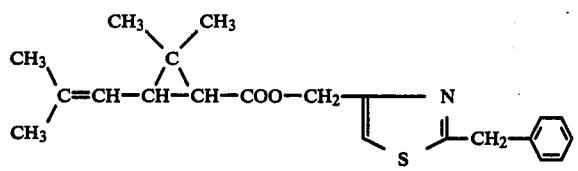

OBJECTS OF THE INVENTION

It is an object of the invention to provide the novel heterocyclic esters of formula I and a process for their preparation.

It is another object of the invention to provide novel pesticidal compositions and a novel method of combatting pests.

These and other objects and advantages of the invention will become obvious from the following detailed description.

THE INVENTION

The novel esters of the invention have the formula

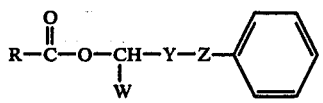

wherein R is selected from the group consisting of

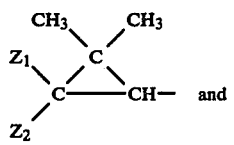 and 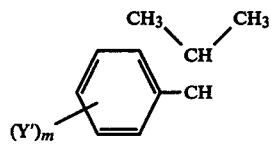

$Z_1$ and $Z_2$ may both be methyl or $Z_1$ is hydrogen and $Z_2$ is

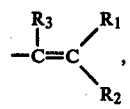

(a) $R_3$ is selected from the group consisting of hydrogen and halogen, $R_1$ and $R_2$ are individually selected from the group consisting of halogen, alkyl of 1 to 8 carbon atoms or taken together with the carbon they are attached to form cycloalkyl of 3 to 6 carbon atoms or

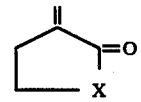

X is selected from the group consisting of NH, oxygen and sulfur or (b) $R_1$ is hydrogen, $R_2$ is alkoxy carbonyl of 2 to 7 carbon atoms, $R_3$ is hydrogen and the double bond has E geometry, or $Z_2$ is

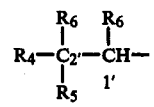

and $R_4$, $R_5$ and $R_6$ are individually halogens, Y' is in any position of the benzene ring and is selected from the group consisting of halogen, alkyl of 1 to 8 carbon atoms and alkoxy of 1 to 8 carbon atoms, m is 0, 1 or 2, W is selected from the group consisting of hydrogen and —CN, Z is selected from the group consisting of —CH$_2$— and —O—, and is attached to a carbon atom included between a nitrogen and the sulfur atom of Y and Y is selected from the group consisting of thiazolyl or thiadiazolyl connected to

at one of its available positions except for α-W-(2-benzyl-4 and 5-thiazolyl)-methyl 2,2-dimethyl-3-(2,2-dimethylethenyl)-cyclopropane -1-carboxylate and α-W-(2-benzyl 5-thiazolyl) methyl 2,2-dimethyl 3-(2,2-dihaloethenyl) cyclopropane 1-carboxylate where W is hydrogen or cyano in all their possible stereoisomer forms.

Examples of $R_1$ and $R_2$ are fluorine, chlorine, bromine, methyl, ethyl, propyl, isopropyl, branched or linear butyl, pentyl, heptyl or octyl or together with the carbon to which they are attached form cyclopropyl, cyclobutyl, cyclopentyl or cyclohexyl. $R_3$ may be fluorine, chlorine or bromine. When $R_1$ and $R_3$ are hydrogen, $R_2$ is preferably methoxycarbonyl, ethoxycarbonyl or propoxycarbonyl.

$R_4$, $R_5$ and $R_6$ may be fluorine, bromine or chlorine and examples of Y' are fluorine, bromine, chlorine, methyl, ethyl, isopropyl, n-propyl, branched or linear butyl, pentyl, hexyl, heptyl or octyl, methoxy, ethoxy, propoxy, isopropoxy, branched or linear butoxy, pentoxy, hexyloxyl, heptyloxy or octyloxy.

Among the preferred compounds of the invention are all possible stereoisomers of compounds of the formula

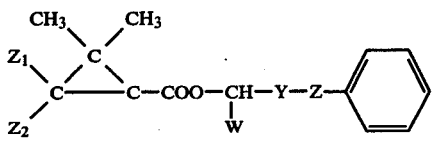

wherein $Z_1$ and $Z_2$ have the above definition, W is hydrogen, Y is

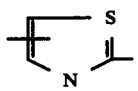

and Z is oxygen (compound A). A more preferred group of compounds of the invention are those of formula $I_A$ wherein $Z_1$ is hydrogen and $Z_2$ is

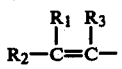

and $R_1$, $R_2$ and $R_3$ have the above definition which are compounds of formula $I_B$. The compounds of formula $I_C$ are those of formula $I_B$ wherein $R_1$ and $R_2$ are halogen and $R_3$ is hydrogen. Especially preferred are the compounds of formula $I_C$ wherein $R_1$ and $R_2$ are bromine.

Another preferred group of compounds of the invention are all the possible stereoisomers of the formula

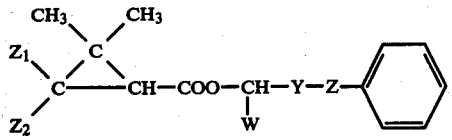

wherein $Z_1$ and $Z_2$ have the above definition, W is —CN, Z is oxygen and Y is

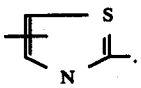

Specific preferred compounds of formula I are (2-phenoxy-4-thiazolyl)-methyl (1R,3R) 2,2-dimethyl-3-(2,2-dibromoethenyl)-cyclopropane-1-carboxylate, (2-phenoxy-5-thiazolyl)-methyl (1R,3R) 2,2-dimethyl-3-(cyclopentylidenemethyl)-cyclopropane-1-carboxylate, (2-phenoxy-5-thiazolyl)-methyl (1R,3S) 2,2-dimethyl-3-(cyclopentylidenemethyl)-cyclopropane-1-carboxylate and (2-phenoxy-5-thiazolyl)-methyl (1R,3S) 2,2-dimethyl-3-(2,2-dibromoethenyl)-cyclopropane-1-carboxylate as well as the other compounds of the examples.

The novel process of the invention for the preparation of the esters of formula I comprises reacting an acid of the formula R—COOH or a functional derivative thereof wherein R has the above definition with an alcohol of the formula

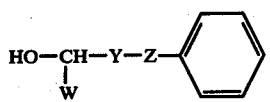

or a functional derivative thereof wherein W, Y and Z have the above definition. The functional acid derivative may be the acid chloride, anhydride or mixed anhydride.

A preferred mode of the process of the invention comprises reacting the acid chloride with the alcohol in the presence of a tertiary base to obtain the desired ester or reacting the acid with the alcohol in an organic solvent in the presence of dicyclohexylcarbodiimide and 4-dimethylamino-pyridine or reacting the acid with the alcohol in the presence of courone ether.

The novel insecticidal compositions of the invention are comprised of an insecticidally effective amount of at least one compound of formula I and an inert carrier. The compositions may be in the form of powders, granules, suspensions, emulsions, solutions, aerosol solutions, combustible bands, baits and other preparations classically used for compounds of this type and may also contain other pesticidal agents.

The compositions have been shown to be useful against houseflies and mosquitoes by their important knockdown and lethal effects. The compounds have also been shown to be useful against *Spodoptera littoralis* and *Epilachna varivestris*.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid such as tabu powder or pyrethrum powder. The insecticidal compositions usually contain 0.055 to 10% by weight of the compounds of formula I.

To increase the insecticidal activity of the compositions of the invention classical synergists may be incorporated therein such as 1-(2,5,8-trioxadodecyl)-2-propyl-4,5-methylenedioxy-benzene (piperonyl butoxide) or N-(2-ethylheptyl)-bicyclo-[2,2-1] 5-heptene-2,3-dicarboximide or piperonyl-bis-2-(2'-n-butoxy-ethoxy)-ethyl acetal (tropital).

The compositions have also been shown to possess acaricidal activity as tests have shown them to be effective against Tetranychus urticae. They possess a dual activity against acariens, the classical lethal activity and a repulsive activity which is interesting from an ecological view. The compositions are useful for combattting vegetable acarien parasites and to repulse them from vegetables.

The acaricidal compositions of the invention are comprised of at least one compound of formula I and an inert carrier and may contain other pesticidal agents or synergists. The compositions may be in the form of powders, granules, suspensions, emulsions or solutions.

For acaricide use, the compositions are preferably in the form of wettable powders for foliar spraying containing 1 to 80% by weight of the active ingredient or as liquids for foliar spraying containing 1 to 500 g/l of active ingredient. Equally useful are powders for foliar powdering containing 0.05 to 10% by weight of the active compound. They are usually applied at 1 to 100 g per hectare.

The novel nematocidal compositions of the invention are comprised of a nematocidally effective amount of at least one compound of formula I and an inert carrier and may also contain other pesticidal agents. The compositions have been shown to be useful against *Panagrellus silusiae*. The nematocidal compositions are preferably in the form of liquids to treat soil containing 300 to 500 g/l of the active ingredient. The compositions are applied at a rate of 1 to 100 g per hectare of the active ingredients.

The fungicidal compositions of the invention are comprised of a fungicidally effective amount of at least one compound of formula I and an inert carrier and optionally other pesticidal agents. The compositions have been shown to be effective against *Botrytis cinerea* and *Fusarium roseum*. The fungicidal compositions are preferably in the form of powders for folira spraying containing 25 to 95% by weight of the active ingredient or powders for foliar powdering containing 2.5 to 99% by weight of the active ingredient.

The compositions of the invention also are useful to combat animal acarien parasites and may be used in veterinary compositions to combat ticks and sarcoptides animal parasites. Tests have shown them to be effective against *Rhipicephalus sanguineus* in dog.

The animal acaricides are useful to combat all types of scabies such as sarcoptic scabies, psoroptic scabies and chorioptic scabies. They may be used to combat all types of ticks such as Boophilus species, Hyalomnia species, Amblyoma species and Rhipicephalus species.

The veterinary compositions of the invention may be used to combat affections provoked by acariens and may be used externally or parenterally or orally or rectally. The veterinary compositions may also advantageously contain a pyrethrinoid synergist.

The compositions for veterinary use may also be made by incorporating a compound of formula I into animal feeds for the specific animal. For example, the animal feed may contain 0.01 to 2% by weight of (2-phenoxy-4-thiazolyl)-methyl (1R,3S) 2,2-dimethyl-3-[(dihydro-2-oxo-3-(2H)-thienylidene)-methyl]-cyclopropane-1-carboxylate.

The pesticidal compositions of the invention may contain besides the compounds of formula I as the active ingredient also at least one pyrethrinoid ester selected from the group consisting of esters of chrysanthemic acids and allethrolones, 3,4,5,6-tetrahydrophthalimido-methanol, 5-benzyl-3-furyl-methanol, 3-phenoxy-benzyl alcohol and α-cyano-3-phenoxy benzyl alcohols, esters of 5-benzyl-3-furylmethanol and 2,2-dimethyl-3-(2-oxo-3-tetrahydrothiophenylidene methyl)-cyclopropane-1-carboxylic acids, esters of 2,2-dimethyl-3-(2,2-dichlorovinyl)-cyclopropane-1-carboxylic acids and 3-phenoxy-benzyl alcohol and α-cyano-3-phenoxy-benzyl alcohols, esters of α-cyano-3-phenoxy-benzyl alcohols and 2,2-dimethyl-3-(2,2-dibromovinyl)-cyclopropane-1-carboxylic acids, esters of 3-phenoxy-benzyl alcohol and 2-p-chlorophenyl-2-isopropylacetic acids, esters of allethrolones, 3,4,5,6-tetrahydrophthalimido-methanol, 5-benzyl-3-furyl-methanol, 3-phenoxybenzyl alcohols and α-cyano-3-phenoxy-benzyl alcohols and 2,2-dimethyl-3-(1,2,2,2-tetrahaloethyl)-cyclopropane-1-carboxylic acids wherein the halogens are fluorine, chlorine and/or bromine with the compounds existing in all possible stereoisomer forms as well as the acid moieties and the alcohol moieties of the pyrethrinoid esters. The said associations are interesting as they have a polyvalent activity against a large spectrum of parasites or have in certain cases a synergist effect.

The novel method of combatting pests comprises contacting pests with a pesticidally effective amount of at least one compound of formula I.

The alcohols used to prepare the esters of formula I are known or are described in copending, commonly assigned U.S. patent application Ser. No. 352,256 filed on even date herewith.

Among the preferred alcohols are those wherein W is hydrogen, Y is

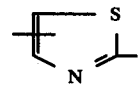

and Z is oxygen, those wherein W is hydrogen, Y is

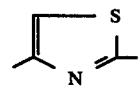

and Z is —CH$_2$— except (2-benzyl -5-thiazolyl)-methanol and those wherein W is —CN, Y is

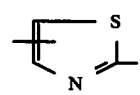

and Z is —O—.

The preparation of an alcohol wherein W is hydrogen, X is —OH, Z is —CH$_2$— and Y is

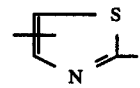

or (2-benzyl-4-thiazolyl)-methanol comprises reacting ethyl bromopyruvate and phenyl thioacetamide to obtain ethyl 2-benzyl-thiazole-4-carboxylate and reacting the latter with a reducing hydride to obtain the corresponding compound of formula I.

The preparation of an alcohol wherein W is hydrogen, X is —OH, Z is —O— and Y is

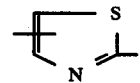

comprises reacting an alkali metal phenate with a compound of the formula

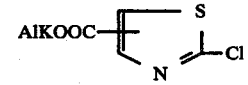

wherein AlK is alkyl of 1 to 6 carbon atoms to obtain a compound of the formula

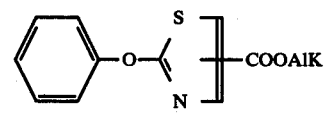   A and reacting the latter with a reducing hydride to obtain the corresponding compound of formula I.

The preparation of an alcohol wherein W is hydrogen, X is —Cl, Z is —O— and Y is

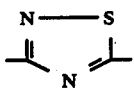

or 3-chloromethyl-5-phenoxy-(1,2,4)-thiadiazole comprises reacting an alkali metal phenate and 3-chloromethyl-5-chloro-(1,2,4)-thiadiazole.

The preparation of an alcohol wherein W is hydrogen, Z is —O—, X is —Cl and Y is

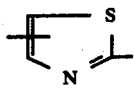

comprises reacting an alkali metal phenate and the corresponding 2-chloro compounds.

The preparation of an alcohol wherein W is hydrogen, X is —Cl, Z is —CH$_2$— and Y is

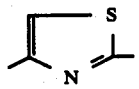

comprises reacting dichloroacetone and phenyl thioacetamide to obtain a compound of the formula

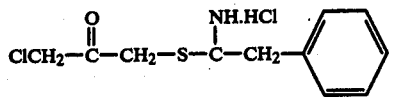

B and cyclizing the latter with concentrated sulfuric acid.

The preparation of an alcohol wherein W is hydrogen, X is —Cl, Z is —CH$_2$— and Y is

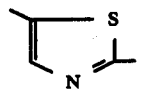

comprises reacting (2-benzyl-5-thiazolyl)-methanol with phosphorus pentachloride or phosphorus oxychloride.

The preparation of an alcohol wherein W is hydrogen, X is —Cl, Z is —CH$_2$— and Y is

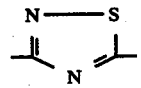

comprises reacting chloroacetamidine hydrochloride and ethyl phenylthioacetate in the presence of sodium ethylate.

The preparation of an alcohol wherein W is hydrogen, X is —OH, Z is —O— or —CH$_2$— and Y is

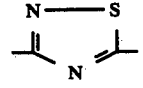

comprises subjecting the corresponding 3-chloromethyl compound to acid or basic hydrolysis.

The preparation of an alcohol wherein X is iodine or bromine comprises heating the corresponding chloro compound with potassium iodide or potassium bromide.

The preparation of an alcohol of the formula

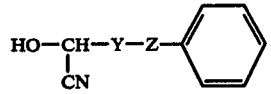

wherein Y and Z have the above definition comprises reacting a compound of the formula

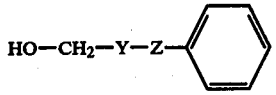

with manganese dioxide to obtain a compound of the formula

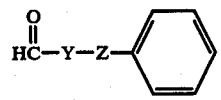

and reacting the latter in an aqueous acid medium with a compound capable of generating CN$^-$ ions.

In preferred embodiments of the processes of the invention, the reducing hydride in diethyl sodium aluminum dihydride and the alkali metal phenate is sodium phenate or potassium phenate. The AlK in the compound of formula A is preferably ethyl and the generation of the CN$^-$ ions is effected with an alkali metal cyanide in the presence of an acid. The hydrolysis of the 3-chloromethyl compounds is effected with a base such as sodium carbonate or potassium carbonate or sodium hydroxide or potassium hydroxide or an acid such as hydrochloric acid.

In the following examples there are described several preferred embodiments to illustrate the invention. However, it is to be understood that the invention is not intended to be limited to the specific embodiments.

EXAMPLE 1

(2-benzyl-4-thiazolyl)-methyl (1R,3S) 2,2-dimethyl-3-[(dihydro-2-oxo-3-(2H)-thienylidene)-methyl]-cyclopropane-1-carboxylate Step A: Ethyl 2-benzyl-thiazole-4-carboxylate 40 g of allyl bromopyruvate were progressively added to a mixture of 30.2 g of phenylthioacetamide, 120 ml of ethanol and 20 ml of pyridine and the mixture was refluxed for 16 hours. The mixture was evaporated to dryness under reduced pressure and the residue was added to a water-ether mixture. The mixture was stirred and the decanted aqueous phase was extracte with ether. The combined organic phases were evaporated to dryness and the residue was chromatographed over silica gel. Elution with a 7-3 hexane-ethyl acetate mixture yielded 22.5 g of ethyl 2-benzyl-thiazole-4-carboxylate melting at 78°-79° C.

Step B: (2-benzyl-4-thiazolyl)-methanol 90 ml of a toluene solution of 2 M/liter of diethyl sodium aluminum dihydride was added dropwise at −10° C. to a solution of 20 g of the product of Step A in 100 ml of toluene and the mixture was stirred at −5° C. for one hour. 150 ml of aqueous 2N hydrochloric acid were added dropwise to the mixture at −20° C. and then ether and water were added thereto. The mixture was filtered and the organic phase of the filtrate was washed with water, dried and evaporated to dryness. The residue was chromatographed over silica gel and was eluted with a 7-3 methylene chloride-ethyl acetate mixture to obtain 13.6 g of (2-benzyl-4-thiazolyl)-methanol melting about 50° C.

IR Spectrum (Chloroform): Absorption at 3595 cm$^{-1}$ (OH); at 1690, 1616 and 1586 cm$^{-1}$ (C=C, C=N and aromatic ring); at 1568, 1536 and 1487 cm$^{-1}$ (aromatic ring).

Step C: (2-benzyl-4-thiazolyl)-methyl (1R,3S) 2,2-dimethyl-3-[(dihydro-2-oxo-3-(2H)-thienylidene)-methyl]-cyclopropane-1-carboxylate 1.05 g of dicyclohexylcarbodiimide was added to a solution of 1.22 g of (1R,3S) 2,2-dimethyl-3-[(dihydro-2-oxo-3-(2H)-thienylidene)-methyl]-cyclopropane-1-carboxylic acid, 0.1 g of 4-dimethylamino-pyridine and 15 ml of methylene chloride and the mixture was stirred at 20° C. for 15 minutes and was cooled to 10° C. A solution of 1 g of the product of Step B in 10 ml of methylene chloride was added dropwise to the mixture which was stirred at room temperature for 2 hours and was filtered. The organic filtrate was evaporated to dryness under reduced pressure and the residue was chromatographed over silica gel. Elution with a 7-3 hexane-ethyl acetate mixture yielded 1.4 g of (2-benzyl-4-thiazolyl)-methyl (1R,3S) 2,2-dimethyl-3-[(dihydro-2-oxo-3-(2H)-thienylidenemethyl]-cyclopropane-1-carboxylate melting at 98° C. and having a specific rotation of $[\alpha]_D^{20} = +15.7° \pm 1.5°$ (c=0.9% in benzene).

EXAMPLE 2

(2-benzyl-5-thiazolyl)-methyl (1R,3R) 2,2-dimethyl-3-[2,2-dibromoethenyl]-cyclopropane-1-carboxylate A solution of 1.26 g of (1R,3R) 2,2-dimethyl-3-(2,2-dibromoethenyl)-cyclopropane-carboxylic acid chloride in 8 ml of benzene was added with stirring at 5° C. to a solution of 0.8 g of (2-benzyl-5-thiazolyl)-methanol in 8 ml of benzene and 0.8 ml of pyridine and the mixture was stirred at 20° C. for 17 hours and was poured into aqueous 2N hydrochloric acid solution with stirring. The decanted organic phase was washed with water and evaporated to dryness under reduced pressure. The residue was chromatographed over silica gel and eluted with a 7-3 hexane-ethyl acetate mixture to obtain 1.41 g of (2-benzyl-5-thiazolyl)-methyl (1R,3R) 2,2-dimethyl-3-[2,2-dibromoethenyl]-cyclopropane-1-carboxylate melting at 66° C. and having a specific rotation of $[\alpha]_D^{20} = +9° \pm 1°$ (c=1% in benzene).

EXAMPLE 3

(2-benzyl-5-thiazolyl)-methyl (1R,3S) 2,2-dimethyl-3-[(dihydro-2-oxo-3-(2H)-thienylidene)-methyl]-cyclopropane-1-carboxylate 0.1 g of 4-dimethylamino-pyridine and 0.94 g of dicyclohexylcarbodiimide were added to a solution of 1.1 g of (1R,3S) 2,2-dimethyl-3-[(dihydro-2-oxo-3-(2H)-thienylidene)-methyl]-cyclopropane-1-carboxylic acid in 10 ml of methylene chloride and then a solution of 1 g of (2-benzyl-5-thiazolyl)-methanol in 12 ml of methylene chloride was added to the mixture. The mixture was stirred for 17 hours at 20° C. and was filtered and the organic filtrate was washed with water, dried and evaporated to dryness under reduced pressure. The residue was taken up in 8 ml of a 7-3 cyclohexane-ethyl acetate mixture and the mixture was filtered. The filtrate was chromatographed over silica gel and was eluted with a 7-3 cyclohexane-ethyl acetate mixture to obtain 0.97 g of (2-benzyl-5-thiazolyl)-methyl (1R,3S) 2,2-dimethyl-3-[(dihydro-2-oxo-3-(2H)-thienylidene)-methyl]-cyclopropane-1-carboxylate with a specific rotation of $[\alpha]_D^{20} = +38° \pm 2°$ (c=0.5% in benzene).

EXAMPLE 4

(2-phenoxy-4-thiazolyl)-methyl (1R,3R) 2,2-dimethyl-3-(2,2-dibromoethenyl)-cyclopropane-1-carboxylate

Step A: Ethyl 2-phenoxy-thiazole-4-carboxylate

A mixture of 2 g of ethyl 2-chloro-thiazole-4-carboxylate, 2.5 ml of hexamethylphosphorotriamide, 50 ml of dimethylformamide and 1.5 g of sodium iodide was heated at 100° C. for one hour and was cooled to 20° C. 1.32 g of potassium phenate were added in portions to the mixture which was then refluxed for 90 minutes and then was cooled. Water and ethyl acetate were added to the mixture and the decanted aqueous phase was extracted with ethyl acetate. The organic phase was washed with water and evaporated to dryness. The residue was chromatographed over silica gel and was eluted with a 7-3-1 hexane-isopropyl ether-triethylamine mixture to obtain 1.08 g of ethyl 2-phenoxy-thiazole-4-carboxylate melting at 67° C.

Step B. (2-phenoxy-4-thiazolyl)-methanol 54 ml of a toluene solution of 2 M/liter of diethyl sodium aluminum dihydride were slowly added at 20° C. to a solution of 12 g of ethyl 2-phenoxy-thiazole-carboxylate in 60 ml of toluene and the mixture were stirred at −5° C. for one hour. 80 ml of aqueous 2N hydrochloric acid were added at −20° C. to the mixture followed by addition of water and filtration. The decanted organic phase was washed with water and evaporated to dryness. The residue was chromatographed over silica gel and eluted with an 8-2 methylene chloride-ethyl acetate mixture to obtain 8.15 g of (2-phenoxy-4-thiazolyl)-methanol).

IR Spectrum (chloroform): Absorption at 3590 cm$^{-1}$ (OH); at 1551, 1530, 1503 and 1486 cm$^{-1}$ (aromatic ring and thiazolyl); at 690 cm$^{-1}$ (phenyl-deformation).

NMR Spectrum (deuterchloroform): Peaks at 4.5 ppm (hydrogens of CH$_2$O); at 3.5 ppm (hydrogen of —OH); at 6.66 ppm (hydrogen of thiazole); at 7.10 to 7.50 ppm (hydrogens of aromatic ring).

Step C: (2-phenoxy-4-thiazolyl)-methyl (1R,3R) 2,2-dimethyl-3-(2,2-dibromoethenyl)-cyclopropane-1-carboxylate 1.6 ml of pyridine was added dropwise at 0° C. to a solution of 1.7 g of (1R,3R) 2,2-dimethyl-3-[2,2-dibromoethenyl]-cyclopropane-1-carboxylic acid chloride and 1 g of the product of Step B in 20 ml of benzene and the mixture was stirred for 2 hours at 20° C. and was poured into aqueous N hydrochloric acid solution.

The decanted organic phase was washed with water, dried and evaporated to dryness. The residue was chromatographed over silica gel and was eluted with a 9–1 hexane-ethyl acetate mixture to obtain 1.87 g of (2-phenoxy-4-thiazolyl)-methyl (1R,3R) 2,2-dimethyl-3-(2,2-dibromoethenyl)-cyclopropane-1-carboxylate melting at ≃50° C. and having a specific rotation of $[\alpha]_D^{20} = -9° \pm 1°$ (c=1% in benzene).

EXAMPLE 5

(2-phenoxy-4-thiazolyl)-methyl (1R,3S) 2,2-dimethyl-3-[(dihydro-2-oxo-3-(2H)-thienylidene)-methyl]-cyclopropane-1-carboxylate 0.11 g of 4-dimethylamino-pyridine and 2 g of dicyclohexylcarbodiimide was added to a solution of 2.04 g of (1R,3S) 2,2-dimethyl-3-[(dihydro-2-oxo-3-(2H)-thienylidene)-methyl]-cyclopropane-1-carboxylic acid [described in French Pat. No. 70-21682] in 20 ml of methylene chloride and the mixture was stirred at 20° C. for 15 minutes. A solution of 1.7 g of (2-phenoxy-4-thiazolyl)-methanol in 10 ml of methylene chloride was added dropwise to the mixture which was stirred at 20° C. for 17 hours and was filtered. The organic phase of the filtrate was washed with water, dried and evaporated to dryness under reduced pressure. The residue was chromatographed over silica gel and was eluted with an 8–2 cyclohexane-ethyl acetate mixture to obtain 2.44 g of (2-phenoxy-4-thiazolyl)-methyl (1R,3S) 2,2-dimethyl-3-[(dihydro-2-oxo-3-(2H)-thienylidene)-methyl]-cyclopropane-1-carboxylate melting at 78° C.

EXAMPLE 6

(2-phenoxy-5-thiazolyl)-methyl (1R,3R) 2,2-dimethyl-3[2,2-dibromoethenyl]-cyclopropane-1-carboxylate Step A: Ethyl 2-phenoxy-thiazole-5-carboxylate A mixture of 3.8 g of ethyl 2-chloro-thiazole-5-carboxylate, 3 g of sodium iodide and 50 ml of acetonitrile was refluxed for one hour and 2.6 g of potassium phenate were added thereto. The mixture was refluxed for 24 hours and concentrated. Water was added to the mixture which was then extracted with ethyl acetate. The organic phase was dried and evaporated to dryness. The residue was chromatographed over silica gel and eluted with a 9–1 benzene-ethyl acetate mixture to obtain 3 g of ethyl 2-phenoxy-thiazole-5-carboxylate.

IR Spectrum (chloroform): Absorption at 1710 cm$^{-1}$ (C═O); at 1537 cm$^{-1}$ (C═C and C═N); at 1595–1491 cm$^{-1}$ (aromatic ring).

Step B: (2-phenoxy-5-thiazolyl)-methanol

A solution of 12 g of the product of Step A in 100 ml of tetrahydrofuran was added dropwise to a mixture of 2.8 g of lithium aluminum hydride in 200 ml of tetrahydrofuran and the mixture was refluxed for 24 hours. Excess hydride was destroyed by addition of ethyl acetate and aqueous 2N hydrochloric acid was added thereto. The mixture was filtered and the aqueous phase was extracted with ether. The combined organic phases were evaporated to dryness to obtain 5.2 g of (2-phenoxy-5-thiazolyl)-methanol.

IR Spectrum (chloroform): Absorption at 3590 cm$^{-1}$ (OH); at 1606, 1599, 1500 and 1481 cm$^{-1}$ (aromatic ring and conjugated system).

NMR Spectrum (deuterochloroform): Peaks at 4.64–4.65 ppm (hydrogens of methylene of alcohol); at 4.75 ppm (hydrogen of —OH); at 6.7 to 7.5 ppm (hydrogens of phenyl).

Step C: (2-phenyl-5-thiazolyl)-methyl (1R,3R) 2,2-dimethyl-3-[2,2-dibromoethenyl]-cyclopropane-1-carboxylate 3 ml of pyridine were added dropwise at 5° C. to a solution of 2.1 g of the product of Step B in 50 ml of benzene and 3.5 g of (1R,3R) 2,2-dimethyl-3-[2,2-dibromoethenyl]-cyclopropane-1-carboxylic acid chloride and the mixture was stirred at 20° C. for 8 hours and was poured into aqueous 2N hydrochloric acid. The decanted organic phase was dried and evaporated to dryness under reduced pressure. The residue was chromatographed over silica gel and eluted with a 95–5 benzene-ethyl acetate mixture to obtain 1.45 g of (2-phenoxy-5-thiazolyl)-methyl (1R3R) 2,2-dimethyl-3-[2,2-dibromoethenyl]-cyclopropane-1-carboxylate.

NMR Spectrum (deuterochloroform): Peaks at 1.25–1.27 ppm (hydrogens of geminal methyls); at 1.73–2.27 ppm (3- and 1-hydrogens of cyclopropyl); at 5.1 ppm (hydrogens of —COOCH$_2$—); at 6.65–6.78 ppm (ethylenic hydrogen); at 7.17 to 7.5 ppm (phenyl hydrogens and thiazolyl hydrogen).

EXAMPLE 7

(2-phenoxy-5-thiazolyl)-methyl (1R,3S) 2,2-dimethyl-3-[(dihydro-2-oxo-3-(2H)-thienylidene)-methyl]-cyclopropane-1-carboxylate 2.1 g of (2-phenoxy-5-thiazolyl)-methanol were added to a solution of 2.44 g of (1R,3S) 2,2-dimethyl-3[(dihydro-2-oxo-3-(2H)-thienylidene)-methyl]-cyclopropane-1-carboxylic acid chloride [described in French Pat. No. 70-21682] in 50 ml of benzene and 3 ml of pyridine were added thereto dropwise at 0° C. The mixture was stirred at 20° C. for 24 hours and was then poured into aqueous 2N hydrochloric acid solution. The decanted organic phase was dried and evaporated to dryness under reduced pressure. The residue was chromatographed over silica gel and was eluted with benzene. The product was crystallized from ethyl acetate to obtain 1.8 g of (2-phenoxy-5-thiazolyl)-methyl (1R,3S) 2,2-dimethyl-3-[(dihydro-2-oxo-3-(2H)-thienylidene)-methyl]-cyclopropane-1-carboxylate.

NMR Spectrum (deuterochloroform): Peaks at 1.26–1.33 ppm (hydrogens of geminal methyls); at 1.58–2.07 ppm (1- and 3-hydrogens of cyclopropyl); at 2.83 to 3.47 ppm (hydrogens of oxothienylidene ring); at 5.12 ppm (hydrogens of —CO$_2$—CH$_2$—); at 6.72–6.87 ppm (ethylenic hydrogen); at 7.2–7.42 ppm (thiazolyl hydrogen and phenyl hydrogens).

EXAMPLE 8

(2-phenoxy-5-thiazolyl)-methyl (1R,3R) 2,2-dimethyl-3-cyclopentylidenemethyl)-cyclopropane-1-carboxylate 2.74 g of (2-phenoxy-5-thiazolyl)-methanol were added to a solution of 2 g of (1R,3R) 2,2-dimethyl-3-(cyclopentylidenemethyl)-cyclopropane-1-carboxylic acid chloride [described in French Pat. No. 74405 published under No. 1,505,423] in 30 ml of benzene and 0.81 ml of pyridine was added dropwise thereto. The mixture was stirred at 20° C. for 20 hours and was poured into dilute aqueous hydrochloric acid. The decanted aqueous phase was extracted with ether and the combined organic phases were dried and evaporated to dryness under reduced pressure. The residue was chromatographed over silica gel and was eluted with an 8-2 cyclohexane-ethyl acetate mixture to obtain 1.9 g of (2-phenoxy-5-thiazolyl)-methyl (1R,3R) 2,2-dimethyl-3-(cyclopentylidenemethyl)-cyclopropane-1-carboxylate melting at 67° C.

EXAMPLE 9

(2-phenoxy-5-thiazolyl)-methyl (1R,3R) 2,2-dimethyl-3-(2-methyl-1-propenyl)-cyclopropane-1-carboxylate 2.07 g of (2-phenoxy-5-thiazolyl)-methanol were added to a solution of (1R,3R) 2,2-dimethyl-3-(2-methyl-1-propenyl)-cyclopropane-1-carboxylic acid chloride prepared from 1.68 g of the corresponding acid in 30 ml of benzene and 1.7 ml of pyridine were slowly added thereto at 10° C. The mixture was stirred at 20° C. for 17 hours and was poured into dilute aqueous hydrochloric acid. The decanted aqueous phase was extracted with ether and the combined organic phases were washed with water, dried and evaporated to dryness under reduced pressure. The residue was chromatographed over silica gel and was eluted with an 8-2 cyclohexane-ethyl acetate mixture to obtain 1.9 g of (2-phenoxy-5-thiazolyl)-methyl (1R,3R) 2,2-dimethyl-3-(2-methyl-1-propenyl)-cyclopropane-1-carboxylate.

NMR Spectrum (deuterochloroform): Peaks at 1.12–1.24 ppm (hydrogens of geminal methyls); at 1.31–1.42 ppm (1-hydrogen of cyclopropyl); at 2.68 ppm (hydrogens of methyls of isopropyl); at 4.78–4.92 ppm (ethylenic hydrogen); at 5.1 ppm (hydrogens of —COOCH$_2$—); at 7.17–7.28 ppm (thiazole hydrogen); at 7.17–7.58 ppm (hydrogens of aromatic ring).

EXAMPLE 10

(2-phenoxy-5-thiazolyl)-methyl (1R,3S) 2,2-dimethyl-3-(2-methyl-1-propenyl)-cyclopropane-1-carboxylate 2.07 g of (2-phenoxy-5-thiazolyl)-methanol were added to a solution of (1R,3S) 2,2-dimethyl-3-(2-methyl-1-propenyl)-cyclopropane-1-carboxylic acid chloride prepared from 1.68 g of the corresponding acid in 20 ml of benzene and 0.81 ml of pyridine were added dropwise thereto. The mixture was stirred at 20° C. for 17 hours and was poured into dilute aqueous hydrochloric acid. The decanted aqueous phase was extracted with ether and the combined organic phases were washed with water, dried and evaporated to dryness under reduced pressure. The residue was chromatographed over silica gel and eluted with an 8-2 cyclohexane-ethyl acetate mixture to obtain 1.6 g of (2-phenoxy-5-thiazolyl)-methyl (1R,3S) 2,2-dimethyl-3-(2-methyl-1-propenyl)-cyclopropane -1-carboxylate.

NMR Spectrum (deuterochloroform): Peaks at 1.18–1.23 ppm (hydrogens of geminal methyls); at 1.55–1.88 ppm (1-hydrogen of cyclopropyl); at 1.63–1.72 ppm (hydrogens of methyls of isopropylidene); at 5.08 ppm (hydrogens of —COOCH$_2$—); at 5.27–5.38 ppm (ethylenic hydrogen); at 7.16–7.3 ppm (thiazole hydrogen); at 7.16–7.5 ppm (aromatic hydrogens).

EXAMPLE 11

(2-phenoxy-5-thiazolyl)-methyl (1R,3R) 2,2-dimethyl-3-[(dihydro-2-oxo-3-(2H)-thienylidene)-methyl]-cyclopropane-1-carboxylate 2 g of (2-phenoxy-5-thiazolyl)-methanol were added to a solution of (1R,3R) 2,2-dimethyl-3-[(dihydro-2-oxo-3-(2H)-thienylidene)-methyl]-cyclopropane-1-carboxylic acid chloride [described in French Pat. No. 70-21682 published under No. 2.097.244] prepared from 2.2 g of the corresponding acid in 30 ml of benzene and 0.81 ml of pyridine were added thereto at −10° C. The reaction mixture was stirred at 20° C. for 17 hours and was poured into aqueous dilute hydrochloric acid. The decanted aqueous phase was extracted with ether and the combined organic phases were washed with water, dried and evaporated to dryness under reduced pressure. The residue was chromatographed over silica gel and was eluted with an 8-2 cyclohexane-ethyl acetate mixture to obtain 2.9 g of (2-phenoxy-5-thiazolyl)-methyl (1R,3R) 2,2-dimethyl-3-[(dihydro-2-oxo-3-(2H)-thienylidene)-methyl]-cyclopropane-1-carboxylate.

NMR Spectrum (deuterochloroform): Peaks at 1.27–1.30 ppm (hydrogens of geminal methyls); at 1.75–1.84 ppm (1-hydrogen of cyclopropyl); at 2.92–3.5 ppm (hydrogens of oxothienylidene); at 5.17 ppm (hydrogens of —COOCH$_2$—); at 6.1–6.27 ppm (ethylenic hydrogen); at 7.22–7.33 ppm (thiazole hydrogen); at 7.17–7.58 ppm (aromatic ring hydrogens).

EXAMPLE 12

(2-phenoxy-5-thiazolyl)-methyl (1R,3S) 2,2-dimethyl-3-(cyclopentylidenemethyl)-cyclopropane-1-carboxylate 3.1 g of (2-phenoxy-5-thiazolyl)-methanol were added to a solution of (1R,3S) 2,2-dimethyl-3-(cyclopentylidenemethyl)-cyclopropane-1-carboxylic acid chloride prepared from 2.9 g of the corresponding acid [described in French Pat. No. 70-00265 published under No. 2.076.204] in 45 ml of benzene and 1.2 ml of pyridine were added dropwise thereto at 10° C. The mixture was stirred at 20° C. for 17 hours and was poured into dilute aqueous hydrochloric acid solution. The decanted aqueous phase was extracted with ether and the combined organic phases were washed with water, dried and evaporated to dryness under reduced pressure. The residue was chromatographed over silica gel and was eluted with a 7-3 hexane-isopropyl ether mixture to obtain 1.3 g of (2-phenoxy-5-thiazolyl)-methyl (1R,3S) 2,2-dimethyl-3-(cyclopentylidenemethyl)-cyclopropane-1-carboxylate melting at less than 50° C.

NMR Spectrum (deuterochloroform): Peaks at 1.18–1.25 ppm (hydrogens of geminal methyls); at 5.12 ppm (hydrogens of —COOCH$_2$—); at 5.46 ppm (ethylenic hydrogen); at 7.23–7.46 ppm (aromatic ring hydrogens and thiazole hydrogen); at 2.25 ppm

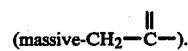

(massive-CH$_2$—$\overset{\parallel}{\text{C}}$—).

EXAMPLE 13

(2-phenoxy-5-thiazoly)-methyl (1R,3S) 2,2-dimethyl-3(2,2-dibromoethenyl)-cyclopropane-1-carboxylate 2 g of (2-phenoxy-5-thiazolyl)-methanol were added to a solution of (1R,3S) 2,2-dimethyl-3-(2,2-dibromoethyenyl)-cyclopropane-1-carboxylic acid chloride prepared from 3 g of the corresponding acid in 50 ml of benzene and 0.81 ml of pyridine were added thereto dropwise at 10° C. The mixture was stirred at 20° C. for 17 hours and was poured into dilute aqueous hydrochloric acid. The decanted aqueous phase was extracted with ether and the combined organic phases were dried and evaporated to dryness under reduced pressure. The residue was chromatographed over silica gel and was eluted with an 8-2 cyclohexane-ethyl acetate mixture to obtain 0.95 g of (2-phenoxy-5-thiazolyl)-methyl (1R,3S) 2,2-dimethyl-3-(2,2-dibromoethenyl)-cyclopropane-1-carboxylate.

NMR Spectrum (deuterochloroform): Peaks at 1.19–1.28 ppm (hydrogens of geminal methyls); at 1.62–1.69 ppm (hydrogen α to COO); at 5.18 ppm (hydrogens of —COOCH$_2$—); at 6.15 ppm and 6.28 ppm (hydrogen of

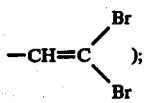

at 7.27–7.37 ppm (thiazole hydrogen); at 2.1–2.18 ppm and 2.23–2.32 ppm (3-hydrogen of cyclopropyl) and 7.25–7.50 ppm (aromatic hydrogens).

EXAMPLE 14

(2-phenoxy-5-thiazoly)-methyl (1R,3S,) 2,2-dimethyl-3-[(E) 3-oxo-3-methoxy-propen-1-yl)-cyclopropane-1-carboxylate 0.1 g of 4-dimethylamino-pyridine and then 0.97 g of dicyclohexylcarbodiimide were added to a solution of 1 g of (1R,3S) 2,2-dimethyl-3-[(E) 3-oxo-3-methoxy-propen-1-yl)-cyclopropane-1-carboxylic acid in 20 ml of methylene chloride and the mixture was stirred at 20° C. for 15 minutes. A solution of 1.24 g of (2-phenoxy-5-thiazolyl)-methanol in 15 ml of methylene chloride was added dropwise at 10° C. to the mixture. The mixture was stirred at 20° C. for 4 hours and was filtered. The filtrate was treated with activated carbon, was washed with water, dried and filtered. The filtrate was evaporated to dryness under reduced pressure and the residue was chromatographed over silica gel. Elution with an 8-2 hexane-ethyl acetate mixture yielded 1.09 g of (2-phenoxy-5-thiazolyl)-methyl (1R,3S) 2,2-dimethyl-3-[(E) 3-oxo-3-methoxy-propen-1-yl)-cyclopropane-1-carboxylate with a specific rotation of $[\alpha]_D^* = +60.5°$ (c=1.5% in benzene) and melting at 62° C.

EXAMPLE 15

[5-phenoxy-(1,2,4)-thiadiazol-3-yl]-methyl (1R,3R) 2,2-dimethyl-3-(2,2-dibromoethenyl)-cyclopropane-1-carboxylate Step A: 3-chloromethyl-5phenoxy-[1,2,4]-thiadiazole 5.8 g of sodium phenate were added to a mixture of 50 ml of benzene, 10 ml of dimethylformamide and 8.5 g of 3-chloromethyl-5-chloro-[1,2,4]-thiadiazole and the mixture was stirred at 20° C. for 24 hours. 50 ml of water were added to the mixture and the decanted aqueous phase was extracted with benzene. The combined organic phase was dried and evaporated to dryness. The oil residue was distilled under reduced pressure to obtain 7.2 g of 3-chloromethyl-5-phenoxy-[1,2,4]-thiadiazole boiling at 114°–116° C. at 0.5 mm Hg.

Step B: [5-phenoxy-(1,2,4)-thiadiazol-3-yl]-methyl (1R,3R) 2,2-dimethyl-3-(2,2-dibromoethenyl)-cyclopropane-1-carboxylate A mixture of 3.3 g of (1R,3R) 2,2-dimethyl-3-(2,2-dibromoethenyl)-cyclopropane-1-carboxylic acid, 2.2 g of the product of Step A, 1.5 g of potassium carbonate, 100 mg of 1,4,7,10,13,16-hexaoxacyclooctadecane and 50 ml of methyl ethyl ketone was refluxed for 24 hours and was evaporated to dryness under reduced pressure. The residue was added to water and the aqueous mixture was extracted with ethyl acetate. The organic phase was evaporated to dryness under reduced pressure and the residue was chromatographed over silica gel. Elution with benzene yielded 2.84 g of [5-phenoxy-(1,2,4)-thiadiazol-3-yl]-methyl (1R,3R) 2,2-dimethyl-3-(2,2-dibromoethenyl)-cyclopropane-1-carboxylate.

NMR Spectrum (deuterochloroform): Peaks at 1.30 ppm (hydrogens of geminal methyls); at 1.83–2.17 ppm (1- and 3-hydrogens of cyclopropyl); at 5.23 ppm (hydrogens of —COOCH$_2$—); at 6.75–7.0 ppm (ethylenic hydrogen); at 7.5 ppm (aromatic hydrogens).

EXAMPLE 16

[5-phenoxy-(1,2,4)-thiadiazol-3-yl]-methyl (1R,3R) 2,2-dimethyl-3-(2-methyl-1-propenyl)-cyclopropane-1-carboxylate A mixture of 4.5 g of 3-chloromethyl-5-phenoxy-(1,2,4)-thiadiazole, 3.7 g of (1R,3R) 2,2-dimethyl-3-(2-methyl-1-propenyl)-cyclopropane-1-carboxylic acid, 50 ml of methyl ethyl ketone, 3.2 g of potassium carbonate and 0.1 g of 1,4,7,10,13,16-hexaoxacyclooctadecane was refluxed for 18 hours and was cooled and filtered. The filtrate was evaporated to dryness under reduced pressure and the residue was chromatographed over silica gel. Elution with benzene yielded 2.2 g of [5-phenoxy-(1,2,4)-thiadiazol-3-yl]-methyl (1R,3R) 2,2-dimethyl-3-(2-methyl-1-propenyl)-cyclopropane-1-carboxylate.

NMR Spectrum (deuterochloroform): Peaks at 1.13–1.27 ppm (hydrogens of geminal methyls); at 1.47–1.57 ppm (1-hydrogen or cyclopropyl); at 1.68–1.7 ppm (hydrogens of methyls of isopropylidene); at 1.98–2.1–2.2 ppm (3-hydrogen of cyclopropyl); at 4.85–4.98 ppm (ethylenic hydrogen); at 5.8 ppm (hydrogens of —COOCH$_2$—); at 7.42 ppm (aromatic hydrogens).

EXAMPLE 17

(R,S)α-cyano-(2-benzyl-5-thiazolyl)-methyl (1R,3R) 2,2-dimethyl-3-(2,2-dibromovinyl)-cyclopropane-1-carboxylate A solution of 1.2 g of (1R,3R) 2,2-dimethyl-3-(2,2-dibromovinyl)-cyclopropane-1-carboxylic acid chloride in 5 ml of ethyl acetate was added at 10° C. to a solution of 0.8 g of (R,S)α-cyano-(2-benzyl-5-thiazolyl)-methanol, 0.8 ml of pyridine and 30 ml of ethyl acetate and the mixture was stirred at 20° C. for 2 hours and was poured into dilute aqueous hydrochloric acid. The decanted organic phase was dried and evaporated to dryness under reduced pressure. The residue was chromatographed over silica gel and was eluted with a 7-3 hexane-ethyl acetate mixture to obtain 0.920 g of (R,S)α-cyano-(2-benzyl-5-thiazolyl)-methyl (1R,3R) 2,2-dimethyl-3-(2,2-dibromovinyl)-cyclopropane-1-carboxylate.

NMR Spectrum (deuterochloroform): Peaks at 1.2 to 1.3 ppm (hydrogens of geminal methyls); at 1.81–1.90 ppm (hydrogen α to COO); at 4.33 ppm (hydrogens of methylene of benzyl); at 6.55 to 6.72 ppm (hydrogen of

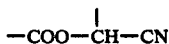

and hydrogen of

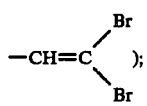

at 7.86 ppm (thiazole hydrogen); at 7.32 ppm (phenyl hydrogens).

EXAMPLE 18

(R,S)α-cyano-(2-benzyl-5-thiazolyl)-methyl (1R,3S) 2,2-dimethyl-3-[(dihydro-2-oxo-3-(2H)-thienylidene)-methyl]-cyclopropane-1-carboxylate A solution of 0.1 g of 4-dimethylamino-pyridine, 0.89 g of dicyclohexylcarbodiimide, 1 g of (1R,3S) 2,2-dimethyl-3-[(dihydro-2-oxo-3-(2H)-thienylidene)-methyl]-cyclopropane-1-carboxylic acid and 20 ml of ethyl acetate was admixed at 10° C. with a solution of 0.9 g (R,S)α-cyano-(2-benzyl-5-thiazolyl)-methanol in 25 ml of ethyl acetate and the mixture was stirred at 10° C. for 2 hours and was filtered. The filtrate was washed with aqueous saturated sodium chloride solution and evaporated to dryness under reduced pressure. The residue was chromatographed over silica gel and eluted with a 6-4 cyclohexane-ethyl acetate mixture to obtain 1.18 g of (R,S) α-cyano-(2-benzyl-5-thiazolyl)-methyl (1R,3S) 2,2-dimethyl-3-[(dihydro-2-oxo-3-(2H)-thienylidene)-methyl]-cyclopropane-1-carboxylate melting at less than 50° C.

NMR Spectrum (deuterochloroform): Peaks at 1.27–1.30–1.37 ppm (hydrogens of geminal methyls); at 1.77–2.05 ppm (hydrogens of cyclopropyl); at 2.83–3.44 ppm (hydrogens of —CH₂—CH₂—S—); at 4.33 ppm (hydrogens of benzyl); at 6.60–6.65 ppm (hydrogen of —COO—CH—CN); at 6.67–6.78 ppm (ethylenic hydrogen); at 7.87 ppm (thiazole hydrogen); at 7.33 ppm (phenyl hydrogen).

EXAMPLE 19

(R,S)α-cyano-(2-benzyl-4-thiazolyl)-methyl (1R,3S) 2,2-dimethyl-3-[(dihydro-2-oxo-3-(2H)-thienylidene)-methyl]-cyclopropane-1-carboxylate

Step A: (2-benzyl-4-thiazolyl)-methanal 2.1 g of manganese dioxide were added to a mixture of 0.5 g of (2-benzyl-4-thiazolyl)-methanol and 10 ml of benzene and the mixture was stirred at 20° C. for 20 hours and was filtered. The filtrate was evaporated to dryness and the residue was chromatographed over silica gel. Elution with a 7-3 hexane-ethyl acetate mixture yielded 0.3 g of (2-benzyl-4-thiazolyl)-methanal melting at 78° C.

Step B: (R,S)α-cyano-(2-benzyl-4-thiazolyl)-methanol

A solution of 2.8 g of the product of Step A in 10 ml of ether was added at 10° C. to a solution of 0.98 g of sodium cyanide in 5 ml of water and the mixture was stirred at 10° C. for 10 minutes. Then, a solution of 2 ml of concentrated sulfuric acid in 3 ml of water was added dropwise to the mixture of 0° C. and the mixture was stirred at 0° C. for 2 hours. Water and ethyl acetate were added to the mixture and the decanted organic phase was washed with water, dried and evaporated to dryness under reduced pressure. The residue was added ot hexane and the mixture was stirred for one hour and was vacuum filtered. The precipitate was dried to obtain 2.76 g of (R,S)α-cyano-(2-benzyl-4-thiazolyl)-methanol melting at 98° C.

Step C: (R,S)α-cyano-(2-benzyl-4-thiazolyl)-methyl (1R,3S) 2,2-dimethyl-3-[(dihydro-2-oxo-3-(2H)-thienylidene)-methyl]-cyclopropane-1-carboxylate 0.1 g of 4-dimethylamino-pyridine and then 0.76 g of dicyclohexylcarbodiimide were added to a solution of 0.88 g of (1R,3S) 2,2-dimethyl-3-[(dihydro-2-oxo-3-(2H)-thienylidene)-methyl]-cyclopropane-1-carboxylic acid in 20 ml of methylene chloride and the mixture was stirred at 20° C. for 15 minutes. A solution of 0.8 g of the product of Step B in 15 ml of methylene chloride was added at 10° C. to the mixture which was stirred at 20° C. for 5 hours and was filtered. The filtrate was washed with water, dried and evaporated to dryness under reduced pressure. The residue was chromatographed over silica gel and was eluted with a 7-3 cyclohexane-ethyl acetate mixture to obtain 1.14 g of (R,S)α-cyano-(2-benzyl-4-thiazolyl)-methyl (1R,3S) 2,2-dimethyl-3-[(dihydro-2-oxo-3-(2H)-thienylidene)-methyl]-cyclopropane-1-carboxylate.

NMR Spectrum (deuterochloroform): Peaks at 1.28–1.31–1.38 ppm (hydrogens of geminal methyls); at 1.83 to 2.17 ppm (1- and 3-hydrogens of cyclopropyl); at 2.83–3.5 ppm (hydrogens of

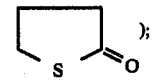

at 4.33 ppm (hydrogens of methylene of benzyl); at 6.43–6.47 ppm (hydrogen on carbon attached to —CN); at 6.65–6.75 ppm (ethylenic hydrogen); at 7.42 ppm (thiazole hydrogen); at 7.3 ppm (phenyl hydrogen).

EXAMPLE 20

(R,S)α-cyano-(2-phenoxy-5-thiazolyl)-methyl (1R,3R) 2,2-dimethyl-3-(2,2-dibromovinyl)-cyclopropane-1-carboxylate

Step A: (2-phenoxy-5-thiazolyl)-methanal 40 g of manganese dioxide were added to a solution of 10 g of (2-phenoxy-5-thiazolyl)-methanol in 250 ml of benzene and the mixture was stirred at 40° C. for 5 hours and was filtered. The filtrate was evaporated to dryness and the residue was chromatographed over silica gel. Elution with a 7-3 methylene chloride-ethyl acetate mixture yielded 7.7 g of (2-phenoxy-5-thiazolyl)-methanal melting at 50° C.

Step B: (R,S)α-cyano-(2-phenoxy-5-thiazolyl)-methanol

A solution of 1.7 g of the product of Step A in 6 ml of ether was added at 15° C. to a solution of 0.6 g of sodium cyanide in 10 ml of water and then a solution of 1 ml of aqueous concentrated sulfuric acid in 0.8 ml of water was added dropwise at 5° C. to the mixture. The mixture was stirred at 10° C. for 2 hours and the decanted organic phase was washed with water, dried and evaporated to dryness. The residue was chromatographed over silica gel and eluted with an 8-2 methylene chloride-ethyl acetate mixture to obtain 1.15 g of (R,S)α-cyano-(2-phenoxy-5-thiazolyl)-methanol.

IR Spectrum (chloroform): Absorption at 1665 cm$^{-1}$ (C=O); at 3580 cm$^{-1}$ (OH); at 3560 cm$^{-1}$ (associated OH); at 1590, 1545, 1490 and 1480 cm$^{-1}$ (C=C, C=N and aromatic ring); at 688 cm$^{-1}$ (phenyl).

NMR Spectrum (deuterochloroform): Peaks at 5.57 ppm (hydrogen of —CH—O—); at 5.33 ppm (hydrogens of —OH); at 7.0 to 7.5 ppm (hydrogens of aromatic ring).

Step C: (R,S)α-cyano-(2-phenoxy-5-thiazolyl)-methyl (1R,3R) 2,2-dimethyl-3-(2,2-dibromovinyl)-cyclopropane-1-carboxylate A solution of 0.85 g of (1R,3R) 2,2-dimethyl-3-(2,2-dibromovinyl)-cyclopropane-1-carboxylic acid chloride in 6 ml of benzene was added dropwise at 10° C. to a solution of 0.620 g of the product of Step B in 6 ml of benzene and 0.55 ml of pyridine and the mixture was stirred for 2 hours at 20° C. and was poured into a dilute aqueous hydrochloric acid solution. The decanted organic phase was washed with water, dried and evaporated to dryness under reduced pressure. The residue was chromatographed over silica gel and eluted with an 8-2 hexane-ethyl acetate mixture to obtain 1.03 g of (R,S)α-cyano-(2-phenoxy-5-thiazolyl)-methyl (1R, 3R) 2,2-dimethyl-3-(2,2-dibromovinyl)-cyclopropane-1-carboxylate with a refractive index of $N_D^{22}$=1.594.

EXAMPLE 21

(R,S)α-cyano-(2-phenoxy-5-thiazolyl)-methyl (1R,3S) 2,2-dimethyl-3-[(dihydro-2-oxo-3-(2H)-thienylidene)-methyl]-cyclopropane-1-carboxylate 1.1 g of a solution of 1.1 g of (R,S)α-cyano-(2-phenoxy-5-thiazolyl)-methanol in 10 ml of methylene chloride were added dropwise at 10° C. to a mixture of 1.07 g of (1R, 3S) 2,2-dimethyl-3-[(dihydro-2-oxo-3-(2H)-thienylidene)-methyl]-cyclopropane-1-carboxylic acid, 0.1 g of 4-dimethylaminopyridine, 0.98 g of dicyclohexylcarbodiimide and 10 ml of methylene chloride and the mixture was stirred at 20° C. for 17 hours and was filtered. The filtrate was washed with water, dried and evaporated to dryness under reduced pressure. The residue was chromatographed over silica gel and was eluted with a 7-3 cyclohexane-ethyl acetate mixture to obtain 1.25 g of (R,S)α-cyano-(2-phenoxy-5-thiazolyl)-methyl (1R,3S) 2,2-dimethyl-3-[(dihydro-2-oxo-3-(2H)-thienylidene)-methyl]-cyclopropane-1-carboxylate melting at 80° to 100° C.

EXAMPLE 22

(R,S)α-cyano-(2-phenoxy-4-thiazolyl)-methyl (1R,3R) 2,2-dimethyl-(2,2-dibromoethenyl)-cyclopropane-1-carboxylate STEP A: (2-phenoxy-4-thiazolyl)-methanal 19.1 g of manganese dioxide were added to a solution of 4.6 g of (2-phenoxy-4-thiazolyl)-methanol in 100 ml of benzene and the mixture was stirred at 60° C. for 3 hours and was filtered. The filtrate was evaporated to dryness under reduced pressure and the residue was chromatographed over silica gel. Elution with an 8-2 methylene chloride-ethyl acetate mixture yielded 2.6 g of (2-phenoxy-4-thiazolyl)-methanal melting at 63° C.

Step B:
(R,S)α-cyano-(2-phenoxy-4-thiazolyl)-methanol

A solution of 2.4 g of product of Step A in 10 ml of ether was added at 10° C. to a solution of 0.85 g of sodium cyanide in 5 ml of water and the mixture was stirred for 10 minutes. A solution of 2 ml of aqueous concentrated sulfuric acid in 3 ml of water was added dropwise at 0° C. to the mixture which was then stirred for 2 hours at 0° C. The decanted organic phase was washed with water, dried and evaporated to dryness under reduced pressure. The residue was added to isopropyl ether and the mixture was vacuum filtered. The product was dried to obtain 2.28 g of (R,S)α-cyano-(2-phenoxy-4-thiazolyl)-methanol.

IR Spectrum (chloroform): Absorption at 3580 cm$^{-1}$ (OH); at 3550 cm$^{-1}$ (associated OH); at 1590, 1504 and 1487 cm$^{-1}$ (aromatic ring and thiazole).

NMR Spectrum (deuterochloroform): Peaks at 4.08 ppm (hydrogen of OH); at 5.41 ppm (hydrogen of >CH—O—); at 7.33 ppm (phenyl hydrogens); at 7.0 ppm (hydrogen of thiazolyl).

Step C: (R,S)α-cyano-(2-phenoxy-4-thiazolyl)-methyl (1R,3R) 2,2-dimethyl-3-(2,2-dibromoethenyl)-cyclopropane-1-carboxylate 0.7 g of the product of Step B were added to a solution of 1.05 g of (1R,3R) 2,2-dimethyl-3-(2,2-dibromoethenyl)-cyclopropane-1-carboxylic acid chloride in 20 ml of acetone and the mixture was stirred for 15 minutes at 20° C. 1.1 ml of pyridine was added to the mixture dropwise at 0° C. and the mixture was stirred at 20° C. for 24 hours and was poured into aqueous dilute hydrochloric acid solution. The decanted organic phase was dried and evaporated to dryness and the residue was chromatographed over silica gel. Elution with an 8-2 hexane-ethyl acetate mixture yielded 1.16 g of (R,S)α-cyano-(2-phenoxy-4-thiazolyl)-methyl (1R,3R) 2,2-dimethyl-3-(2,2-dibromoethenyl)-cyclopropane-1-carboxylate.

NMR Spectrum (deuterochloroform): Peaks at 1.22-1.28 ppm (hydrogens of geminal methyls); at 6.31-6.45 ppm (hydrogen of

at 6.61-6.75 ppm (hydrogen of

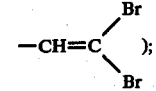

at 7.1 ppm (thiazole hydrogen); at 7.17-7.5 ppm (aromatic hydrogens).

EXAMPLE 23

(R,S)α-cyano-(2-phenoxy-4-thiazolyl)-methyl (1R,3S) 2,2-dimethyl-3-[(dihydro-2-oxo-3-(2H)-thienylidene)-methyl]-cyclopropane-1-carboxylate 0.1 g of 4-dimethylamino-pyridine and then 0.64 g of dicyclohexylcarbodiimide were added to a solution of 0.75 g of (1R,3S) 2,2-dimethyl-3-[(dihydro-2-oxo-3-(2H)-thienylidene)-methyl]-cyclopropane-1-carboxylic acid in 15 ml of methylene chloride and the mixture was stirred for 15 minutes at 20° C. 0.7 g of (R,S)α-cyano-(2-phenoxy-4-thiazolyl)-methanol was added dropwise at 10° C. to the mixture which was stirred for 24 hours at 20° C. and was filtered. The filtrate was washed with water, dried and evaporated to dryness under reduced pressure. The residue was chromatographed over silica gel and eluted with a 7-3 hexane-ethyl acetate mixture and then 9-1 methylene chloride-ethyl acetate to obtain 0.51 g of (R,S)α-cyano-(2-phenoxy-4-thiazolyl)-methyl (1,R3S) 2,2-dimethyl-3-[(dihydro-2-oxo-3-(2H)-thienylidene)-methyl]-cyclopropane-1-carboxylate.

NMR Spectrum (deuterochloroform): Peaks at 1.30–1.37 ppm (hydrogens of geminal methyls); at 6.33–6.42 ppm (hydrogen of CH—CN); at 6.68–6.83 ppm (ethylenic hydrogen); at 7.12 ppm (thiazol hydrogen); at 7.38 ppm (phenyl hydrogen).

EXAMPLE 24

A soluble concentrate was prepared by homogenously mixing 0.25 g of the product of Example 1, 1 g of piperonyl butoxide, 0.25 g of Tween 80, 0.1 g of Topanol A and 98.4 g of water.

An emulsifible concentrate was prepared by intimately mixing 0.015 g of the product of Example 3, 0.5 g of piperonyl butoxide, 0.1 g of Topanol A and 99.385 g of Xylene.

A fumigant composition was prepared by homogeneously mixing 0.25 g of the product of Example 8, 25 g of tabu powder, 40 g of powdered cedar needles, 33.75 g of pine wood powder, 0.5 g of brillant green and 0.5 g of p-nitrophenol.

A veterinary composition for use as a tickicide was prepared from 4 g of the product of Example 8, 2.5 g of piperonyl butoxide, 10 g of Polysorbate 80, 25 g of Triton X100, 1 g of tocopherol acetate and 100 ml of ethanol.

INSECTICIDAL ACTIVITY

A. Lethal effect against houseflies

Female houseflies sensitive to pyrethrinoids 4 to 5 days old at 22°–23° C. and a relative humidity of 60 to 65% received a topical application to the dorsal thorax of 1 μl of an acetone solution of the test compound using an Arnold micromanipulator. 50 insects were used for each test and the number of dead insects were determined 24 hours after treatment. Piperonyl butoxide was used as a synergist at a ratio of 10 parts of synergist per 1 part by weight of test compound and the $DL_{50}$ in nanograms per insect was determined. The compounds of Examples 6 and 16 had a $DL_{50}$ of 14.5 and 17.1 respectively. The compounds of the other examples showed a similar interesting insecticidal activity.

B. Against *Spodoptera littoralis*

The insecticidal activity of the compound of Example 8 was determined by topical application of an acetone solution of the said compound with an Arnold micromanipulator to the dorsal thorax of larvae of *Spodoptera littoralis* using 15 larvae for each dose. The larvae were in the 4th stage of development and were about 10 days old at 24° C. and 65% relative humidity. After treatment, the larvae were placed in an artificial nutritive medium (Poitout medium) and the number of dead larvae was determined 48 hours later to calculate the $DL_{50}$ in manograms per insect. The results are in Table I.

TABLE I

| Compound of Example | $DL_{50}$ in nanogram |
|---|---|
| 2 | 20.4 |
| 5 | 6.0 |
| 6 | 26.6 |
| 9 | 59.2 |
| 10 | 22.5 |
| 13 | 9.2 |
| 15 | 60.2 |
| 21 | 44.5 |
| 23 | 67.6 |

The compounds of the other examples also showed an interesting insecticidal activity in this test.

C. Against Larvae of *Epilachna varivestris*

The test of test B was repeated on larvae of *Epilachna varivestris* in the penultimate stage of larvae development. After treatment the larvae were placed on bean plants for food. The number of dead was determined after 72 hours and the $DL_{50}$ in nanograms per insect was calculated. The results are in Table II.

TABLE II

| Compound of Example | $DL_{50}$ in nanogram |
|---|---|
| 2 | 20.1 |
| 6 | 26.8 |
| 8 | 12.5 |
| 12 | 7.2 |
| 13 | 14.5 |
| 15 | 14.4 |

The compounds of the other examples also showed an interesting insecticidal activity in this test.

D. Knockdown of houseflies

The knockdown activity of the compounds of the Examples against houseflies were determined on female houseflies 4 to 5 days old by direct spraying in one second of 50 insects per dose with 2 ml of a solution of the test product in a mixture of 5% acetone and Isopar L (petroleum solvent) in a Kearns and March cylinder. The readings were taken every minute for 10 minutes and then at 15 minutes and the $KT_{50}$ was determined by known methods. The results are in Table III.

TABLE III

| Compound of Example | $KT_{50}$ |
|---|---|
| 2 | 3.0 |
| 3 | 2.7 |
| 4 | 6.2 |
| 5 | 5.3 |
| 6 | 5.3 |
| 7 | 3.5 |
| 10 | 8.7 |
| 12 | 5.9 |
| 13 | 5.5 |
| 15 | 3.9 |
| 18 | 6.0 |
| 19 | 5.4 |
| 22 | 7.0 |
| 23 | 4.7 |

The compounds of other examples showed an equally interesting knock down activity in the same test.

E. Activity against *Tetranychus urticae*=adulticidal activity test

Bean plants in the two leaf stage were treated with a Fisher pistol at different doses of the test product and after drying, the plants were infested with 25 female *Tetranychus urticae* per leaf and kept at 22°–23° C. and 60–65% relative humidity under permanent artificial light. The number of living and dead acariens was determined 24 and 48 hours after treatment and the compounds of Examples 6 and 10 showed a good adulticidal activity in the test.

Various modifications of the products and processes of the invention may be made without departing from the spirit or scope thereof and it should be understood that the invention is intended to be limited only as defined in the appended claims.

What we claim is:

1. (2-benzyl-5-thiazolyl)-methyl (1R,3S) 2,2-dimethyl-3-[(dihydro-2-oxo-3-(2H)-thienylidene)-methyl]-cyclopropane-1-carboxylate.

2. An insecticidal composition comprising an insecticidally effective amount of the compound of claim 1 and an inert carrier.

3. A method of combating insects comprising contacting insects with an insecticidally effective amount of the compound of claim 1.

* * * * *